United States Patent
Nakamura

(10) Patent No.: US 8,014,582 B2
(45) Date of Patent: Sep. 6, 2011

(54) IMAGE REPRODUCTION APPARATUS AND PROGRAM THEREFOR

(75) Inventor: Keigo Nakamura, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 1216 days.

(21) Appl. No.: 11/653,382

(22) Filed: Jan. 16, 2007

(65) Prior Publication Data

US 2007/0195061 A1 Aug. 23, 2007

(30) Foreign Application Priority Data

Jan. 16, 2006 (JP) ................................ 2006-007631

(51) Int. Cl.
*G06K 9/40* (2006.01)
*G06K 9/46* (2006.01)
*G06K 9/62* (2006.01)

(52) U.S. Cl. ........ 382/132; 382/169; 382/199; 382/203; 382/224; 382/260; 382/274

(58) Field of Classification Search .................. 382/131, 382/132, 169, 170, 199, 203, 209, 217, 224, 382/260–266, 274, 275, 286; 345/698, 699
See application file for complete search history.

(56) References Cited

U.S. PATENT DOCUMENTS

| | | | | | |
|---|---|---|---|---|---|
| 2,455,522 A | * | 12/1948 | Ringler | ........................... | 378/111 |
| 4,903,310 A | * | 2/1990 | Takeo et al. | .................... | 382/132 |
| 4,951,201 A | * | 8/1990 | Takeo et al. | .................... | 382/128 |
| 4,994,355 A | * | 2/1991 | Dickerson et al. | ............. | 430/509 |
| 5,021,770 A | * | 6/1991 | Aisaka et al. | .................. | 345/156 |
| 5,084,908 A | * | 1/1992 | Alberici et al. | .................... | 378/4 |
| 5,345,513 A | * | 9/1994 | Takeda et al. | .................. | 382/132 |
| 5,369,572 A | * | 11/1994 | Haraki et al. | .................... | 378/83 |
| 5,469,353 A | * | 11/1995 | Pinsky et al. | .................. | 382/131 |
| 5,509,042 A | * | 4/1996 | Mazess | ............................. | 378/54 |
| 5,513,101 A | * | 4/1996 | Pinsky et al. | ...................... | 705/3 |
| 5,533,143 A | * | 7/1996 | Takeo | ............................ | 382/132 |

(Continued)

FOREIGN PATENT DOCUMENTS

JP 07-178076 A 7/1995

(Continued)

OTHER PUBLICATIONS

X. Zhou, S. Kobayashi, T. Hayashi, N. Murata, T. Hara, H. Fujita, R. Yokoyama, T. Kiryu, H. Hoshi, M. Sato, "Lung structure recognition: a further study of thoracic organ recognitions based on CT images," Jun. 2003, Computer Assisted Radiology and Surgery. Proc. of the 17th Int. Congress and Exhibition, vol. 1256, pp. 1025-1030.*

(Continued)

*Primary Examiner* — Matthew C Bella
*Assistant Examiner* — Anthony Mackowey
(74) *Attorney, Agent, or Firm* — Sughrue Mion, PLLC

(57) ABSTRACT

A medical image is reproduced after being subjected to image processing appropriate for conversion into an image suitable for interpreting. Selection of a imaging menu item from a imaging menu being displayed is accepted, and the medical image is reproduced after being subjected to the image processing for converting the image into the image appropriate for the reproduction according to the selected imaging menu item. At this time, an index value representing an anatomical characteristic is calculated from the medical image, and the most appropriate imaging menu item to be selected from imaging menu items is judged based on the index value.

7 Claims, 4 Drawing Sheets

U.S. PATENT DOCUMENTS

| | | | | |
|---|---|---|---|---|
| 5,668,888 | A * | 9/1997 | Doi et al. | 382/132 |
| 5,754,676 | A * | 5/1998 | Komiya et al. | 382/132 |
| 5,807,256 | A * | 9/1998 | Taguchi et al. | 600/425 |
| 5,848,198 | A * | 12/1998 | Penn | 382/276 |
| 5,862,249 | A * | 1/1999 | Jang et al. | 382/132 |
| 5,943,435 | A * | 8/1999 | Gaborski | 382/132 |
| 5,987,345 | A * | 11/1999 | Engelmann et al. | 600/407 |
| 6,043,814 | A * | 3/2000 | Lim | 715/700 |
| 6,055,326 | A * | 4/2000 | Chang et al. | 382/132 |
| 6,243,095 | B1 | 6/2001 | Shile et al. | 715/854 |
| 6,278,433 | B2 * | 8/2001 | Narui | 345/581 |
| 6,306,089 | B1 * | 10/2001 | Coleman et al. | 600/437 |
| 6,463,167 | B1 * | 10/2002 | Feldman et al. | 382/128 |
| 6,542,579 | B1 * | 4/2003 | Takasawa | 378/165 |
| 6,585,647 | B1 * | 7/2003 | Winder | 600/437 |
| 6,633,657 | B1 * | 10/2003 | Kump et al. | 382/128 |
| 6,633,684 | B1 * | 10/2003 | James | 382/274 |
| 6,650,924 | B2 * | 11/2003 | Kuth et al. | 600/410 |
| 6,671,394 | B1 * | 12/2003 | Sako | 382/132 |
| 6,697,506 | B1 * | 2/2004 | Qian et al. | 382/128 |
| 6,792,071 | B2 * | 9/2004 | Dewaele | 378/62 |
| 6,859,513 | B2 * | 2/2005 | Sako | 378/16 |
| 6,911,988 | B1 * | 6/2005 | Tsujii | 345/581 |
| 6,954,513 | B2 * | 10/2005 | Horiuchi | 378/4 |
| 7,050,532 | B2 * | 5/2006 | Gohno | 378/8 |
| 7,079,128 | B2 * | 7/2006 | Kim | 345/213 |
| 7,085,407 | B2 * | 8/2006 | Ozaki | 382/132 |
| 7,092,581 | B2 * | 8/2006 | Winsor et al. | 382/274 |
| 7,123,761 | B2 * | 10/2006 | Kawano | 382/132 |
| 7,127,097 | B2 * | 10/2006 | Nagatsuka | 382/132 |
| 7,149,334 | B2 * | 12/2006 | Dehmeshki | 382/131 |
| 7,215,733 | B2 * | 5/2007 | Nabatame | 378/16 |
| 7,215,806 | B1 * | 5/2007 | Bechwati et al. | 382/133 |
| 7,245,747 | B2 * | 7/2007 | Oosawa | 382/128 |
| 7,315,635 | B2 * | 1/2008 | Oosawa | 382/128 |
| 7,324,660 | B2 * | 1/2008 | Oosawa | 382/100 |
| 7,324,673 | B1 * | 1/2008 | Yamanaka et al. | 382/128 |
| 7,359,541 | B2 * | 4/2008 | Kawano | 382/132 |
| 7,369,693 | B2 * | 5/2008 | Shen | 382/128 |
| 7,386,158 | B2 * | 6/2008 | Yamada | 382/132 |
| 7,392,078 | B2 * | 6/2008 | Imai | 600/436 |
| 7,397,475 | B2 * | 7/2008 | Shen et al. | 345/420 |
| 7,421,104 | B2 * | 9/2008 | Hsieh et al. | 382/132 |
| 7,433,507 | B2 * | 10/2008 | Jabri et al. | 382/132 |
| 7,516,417 | B2 * | 4/2009 | Amador et al. | 715/788 |
| 7,522,175 | B2 * | 4/2009 | Morita et al. | 345/619 |
| 7,574,028 | B2 * | 8/2009 | Luo et al. | 382/128 |
| 7,616,818 | B2 * | 11/2009 | Dewaele | 382/199 |
| 7,627,154 | B2 * | 12/2009 | Luo et al. | 382/128 |
| 7,678,049 | B2 * | 3/2010 | Tsoref et al. | 600/437 |
| 7,724,934 | B2 * | 5/2010 | Shinbata | 382/132 |
| 7,724,936 | B2 * | 5/2010 | Oosawa | 382/132 |
| 7,729,524 | B2 * | 6/2010 | Rogers et al. | 382/128 |
| 2002/0010395 | A1 * | 1/2002 | Strawder | 600/407 |
| 2002/0060302 | A1 | 5/2002 | Aonuma | |
| 2002/0072665 | A1 | 6/2002 | Ozaki | |
| 2002/0085743 | A1 * | 7/2002 | Kawano | 382/132 |
| 2003/0053673 | A1 * | 3/2003 | Dewaele | 382/132 |
| 2003/0118226 | A1 * | 6/2003 | Winsor et al. | 382/132 |
| 2003/0215120 | A1 * | 11/2003 | Uppaluri et al. | 382/128 |
| 2004/0151358 | A1 * | 8/2004 | Yanagita et al. | 382/132 |
| 2004/0161141 | A1 * | 8/2004 | Dewaele | 382/132 |
| 2004/0184644 | A1 * | 9/2004 | Leichter et al. | 382/128 |
| 2005/0008206 | A1 * | 1/2005 | Kawano | 382/128 |
| 2005/0008262 | A1 * | 1/2005 | Komiya et al. | 382/305 |
| 2005/0010107 | A1 * | 1/2005 | Shen | 600/425 |
| 2005/0035982 | A1 * | 2/2005 | Hong et al. | 345/698 |
| 2005/0041114 | A1 * | 2/2005 | Kagaya | 348/222.1 |
| 2005/0068252 | A1 * | 3/2005 | Driver et al. | 345/1.1 |
| 2005/0084178 | A1 * | 4/2005 | Lure et al. | 382/294 |
| 2005/0100208 | A1 * | 5/2005 | Suzuki et al. | 382/157 |
| 2005/0238218 | A1 * | 10/2005 | Nakamura | 382/128 |
| 2006/0025671 | A1 * | 2/2006 | Kusunoki | 600/407 |
| 2006/0093199 | A1 * | 5/2006 | Fram et al. | 382/128 |
| 2006/0126909 | A1 * | 6/2006 | Marshall et al. | 382/128 |
| 2006/0188134 | A1 * | 8/2006 | Quist | 382/128 |
| 2006/0274145 | A1 * | 12/2006 | Reiner | 348/62 |
| 2006/0280351 | A1 * | 12/2006 | Luping et al. | 382/128 |
| 2007/0086639 | A1 * | 4/2007 | Sakaida | 382/132 |
| 2007/0110295 | A1 * | 5/2007 | Shen et al. | 382/131 |
| 2007/0223795 | A1 * | 9/2007 | Qing et al. | 382/128 |
| 2008/0049996 | A1 * | 2/2008 | Marshall et al. | 382/128 |
| 2008/0214935 | A1 * | 9/2008 | Levin | 600/442 |

FOREIGN PATENT DOCUMENTS

| | | |
|---|---|---|
| JP | 2003-006661 A | 1/2003 |
| JP | 2004-321457 A | 11/2004 |
| JP | 2005-198887 A | 7/2005 |

OTHER PUBLICATIONS

Disclosed anonymously, "Automatic display resolution adjustment," Dec. 2005, Kenneth Mason Publications Ltd, Research Disclosure Journal, Database No. 500073, pp. 1-2.*

English Language Machine Translation of the Detailed Description of Foreign Patent Document JP 07-178076.*

Notice of Reasons for Rejection, dated Oct. 26, 2010, issued in corresponding JP Application No. 2006-007631, 6 pages in English and Japanese.

* cited by examiner

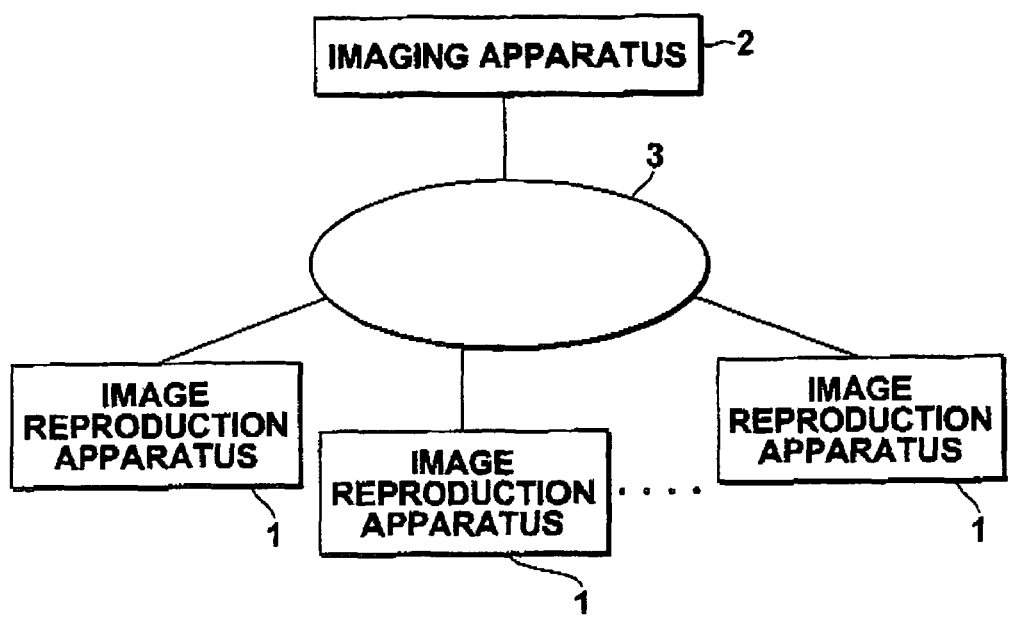
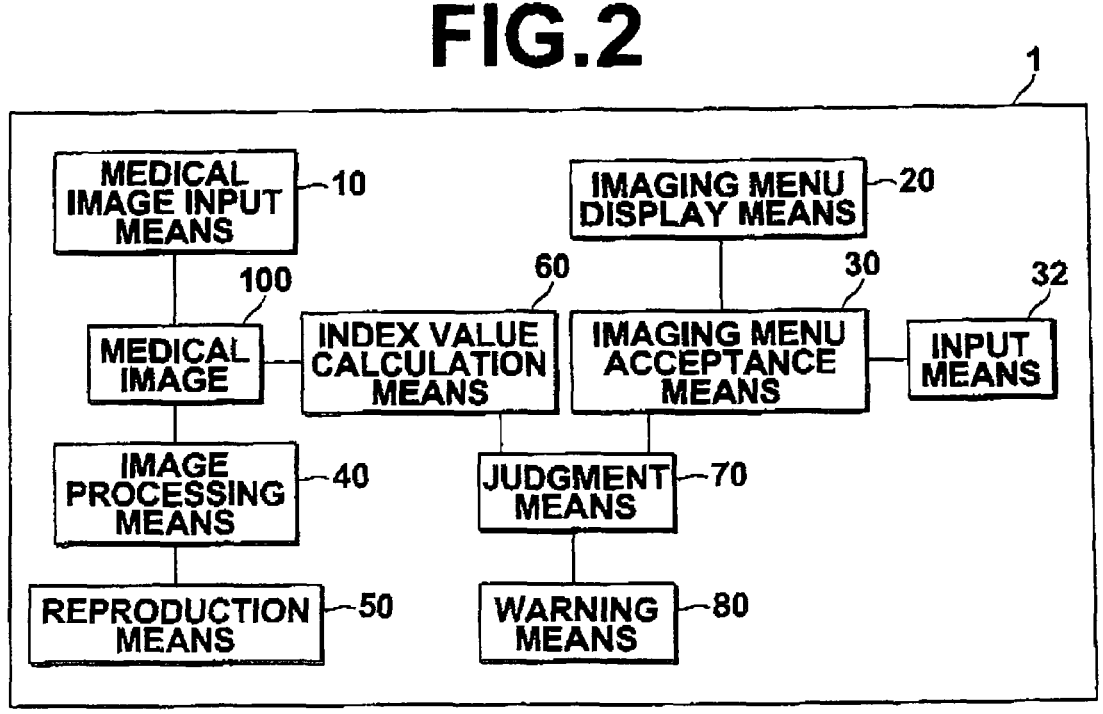

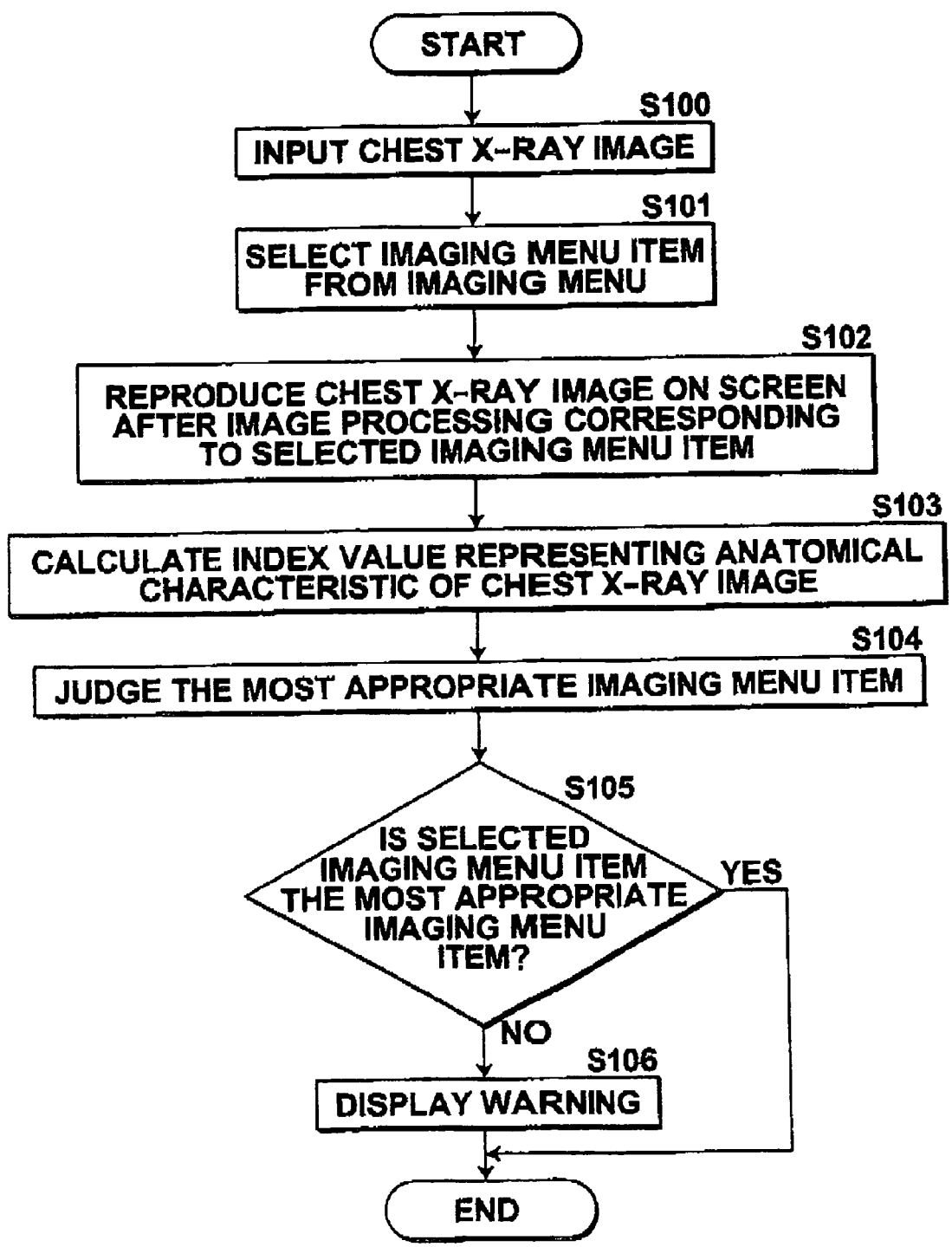

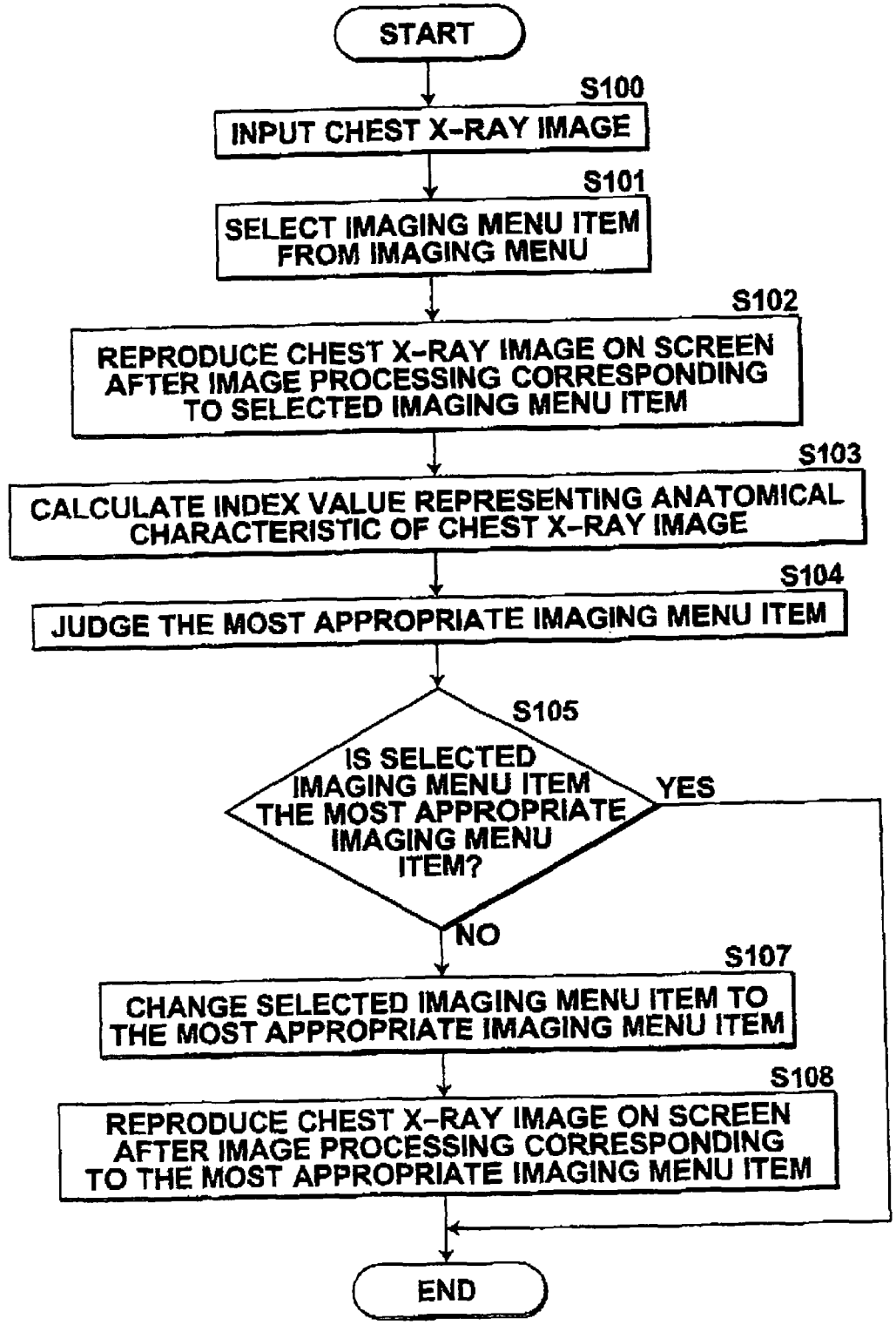

IMAGE REPRODUCTION APPARATUS AND PROGRAM THEREFOR

BACKGROUND OF THE INVENTION

1. Field of the Invention

The present invention relates to an image reproduction apparatus for reproducing medical image and to a program therefor.

2. Description of the Related Art

There have been used radiation image information recording reproducing systems employing stimulable phosphor that stores a part of energy of radiation such as X rays, $\alpha$ rays, $\beta$ rays, $\gamma$ rays, electron rays, and ultraviolet rays emitted thereon and emits light in accordance with the stored energy upon exposure to stimulating rays such as laser beams and visible lights.

Among radiation image information recording reproducing systems of this kind, a system comprising a radiation image reading apparatus, an identification information registration apparatus, and an image recording apparatus is in widespread use. In the radiation image reading apparatus, radiation image information of a patient or the like is once stored in a stimulable phosphor sheet, and the sheet is scanned with a stimulating ray such as a laser beam to cause the stimulable phosphor sheet to emit light. The emitted light is then read photoelectrically to obtain image data. Identification information of the patient is registered in the identification information registration apparatus. The image recording apparatus records a radiation image based on the image data as a visible image on a recording material such as a photosensitive material, while relating the image to the registered identification information of the patient.

In such a conventional radiation image information processing system, a radiation image is displayed on a monitor such as an LCD or CRT for viewing, upon output of a radiation image as a visible image. An image display apparatus of this type tends to be installed at each ward of a hospital, or even for each image interpreter such as a physician or technician. For this reason, not only a hard-copy image output from the system is delivered to each destination such as a ward of a hospital but also a processed radiation image having been subjected to reading, image processing, and the like by a radiation image information reading apparatus is sent to each ward as image data for viewing (display), in order to improve efficiency of diagnosis, to reduce waiting time for patients, and to speed up treatment (see U.S. Patent Application Publication No. 20020060302, for example).

When a radiation image is displayed on a monitor such as an LCD or CRT, various kinds of image processing such as density adjustment processing and enhancement processing is carried out thereon so that the image can be easier to interpret for improving diagnostic performance.

However, if a subject having been graphed is a child or an infant, the contrast of a chest radiation image thereof tends to be less clear than that of a chest radiation image of an adult, due to less air content in the subject's lungs. Therefore, image processing needs to be carried out on the image by using parameters different from those for a chest radiation image of an adult. Consequently, a technician inputs information on a radiation image he/she radiographed, and an image processing apparatus carries out image processing according to the information. However, the number of items to be input is large, and troublesome operations are thus necessary. For this reason, appropriate image processing may not be carried out in some cases due to inaccurate information caused by erroneous input or input omission.

SUMMARY OF THE INVENTION

An object of the present invention is therefore to provide an image reproduction apparatus and a program for enabling image processing appropriate for image reproduction even in the case of erroneous input or input omission of information.

An image reproduction apparatus of the present invention is an image reproduction apparatus comprising medical image input means for inputting a medical image obtained by imaging of a subject, imaging menu display means for displaying a imaging menu including exclusively selectable imaging menu items regarding imaging information of the medical image, imaging menu acceptance means for accepting selection of the imaging menu items from the displayed imaging menu, image processing means for carrying out image processing on the medical image in order to convert the medical image into an image appropriate for reproduction according to the selected imaging menu item accepted by the imaging menu acceptance means, and reproduction means for reproducing the medical image having been subjected to the image processing. The image reproduction apparatus is characterized in that the apparatus further comprises:

index value calculation means for calculating an index value representing an anatomical characteristic from the medical image; and judgment means for judging the most appropriate imaging menu item to be selected from the imaging menu items, based on the calculated index value.

A program of the present invention is a program for causing a computer to function as medical image input means for inputting a medical image obtained by imaging of a subject, imaging menu display means for displaying a imaging menu including exclusively selectable imaging menu items regarding imaging information of the medical image, imaging menu acceptance means for accepting selection of the imaging menu items from the displayed imaging menu, image processing means for carrying out image processing on the medical image in order to convert the medical image into an image appropriate for reproduction according to the selected imaging menu item accepted by the imaging menu acceptance means, and reproduction means for reproducing the medical image having been subjected to the image processing. The program is characterized in that the program further causes the computer to function as:

index value calculation means for calculating an index value representing an anatomical characteristic from the medical image; and judgment means for judging the most appropriate imaging menu item to be selected from the imaging menu items, based on the calculated index value.

The imaging menu refers to a menu related to imaging of the medical image, and the imaging menu items refer to respective items comprising the imaging menu.

The exclusively selectable imaging menu items refer to items of the imaging menu that cannot be selected together. More specifically, imaging menu items included in a imaging menu representing a body part to be imaged are "chest/abdomen", "head", and "breast", for example. Any one of these items can only be selected exclusively, without selecting any of the remaining items. Furthermore, "infant", "toddler", and "child" are listed as imaging menu items for selecting a subject of imaging. Anyone of these items can be selected. Alternatively, all of these items can be not selected. In the latter case, the selected subject is determined to be an "adult", who is not an "infant", or a "toddler", or a "child".

The imaging menu acceptance means may accept the selection of the imaging menu items in the imaging menu being displayed, from predetermined input means. The image reproduction apparatus may further comprise warning means for issuing a warning in the case that a selected imaging menu item is judged not to be the most appropriate imaging menu item.

The imaging menu acceptance means may accept the imaging menu item judged to be most appropriate as the selected imaging menu item.

The image processing may be density adjustment processing.

Alternatively, the image processing may be frequency enhancement processing.

In the case where the medical image is a chest radiograph, the index value may be a size of the thoracic region of the imaged subject.

Alternatively, the index value may be a thickness of a rib of the imaged subject.

According to the present invention, when a user selects one of the imaging menu items corresponding to the medical image from the imaging menu and the medical image is displayed after the image processing appropriate for the selected imaging menu item for causing the image to be easy to interpret has been carried out thereon, the most appropriate imaging menu item is judged for the medical image by using the index value representing the anatomical characteristic of the medical image. In this manner, occurrences of erroneous selections by the user can be decreased, and the image can be displayed after the most appropriate image processing therefor has been carried out thereon.

In the case where the imaging menu item selected by the user does not agree with the most appropriate imaging menu item, the user can be prompted to check the selected imaging menu item again by a warning display or sound, for example.

Alternatively, by accepting the imaging menu item judged to be most appropriate as the selected imaging menu item, the medical image can be displayed as a medical image that is easy to interpret, through the image processing which is expected to be the most appropriate therefor.

By using the density adjustment processing as the image processing, if the medical image is an image of an infant, a toddler, or a child with low contrast, the medical image can be changed to an image with high contrast which is easy to interpret.

Alternatively, the medical image may be changed to an image in which only a target of observation is enhanced by the frequency enhancement processing.

If the medical image is a chest radiograph, the subject can be inferred to be an infant, a toddler, a child, or an adult, by the size of the thoracic region or the thickness of ribs. Therefore, the image processing such as density adjustment for causing the image to become easy to interpret can be carried out.

BRIEF DESCRIPTION OF THE DRAWINGS

FIG. 1 shows the configuration of a medical system;
FIG. 2 shows the configuration of an image reproduction apparatus;
FIG. 4 is a flow chart showing procedures carried out in the image reproduction apparatus (part 1);
and
FIG. 5 is a flow chart showing procedures carried out in the image reproduction apparatus (part 2).

DESCRIPTION OF THE PREFERRED EMBODIMENTS

Figure 3:
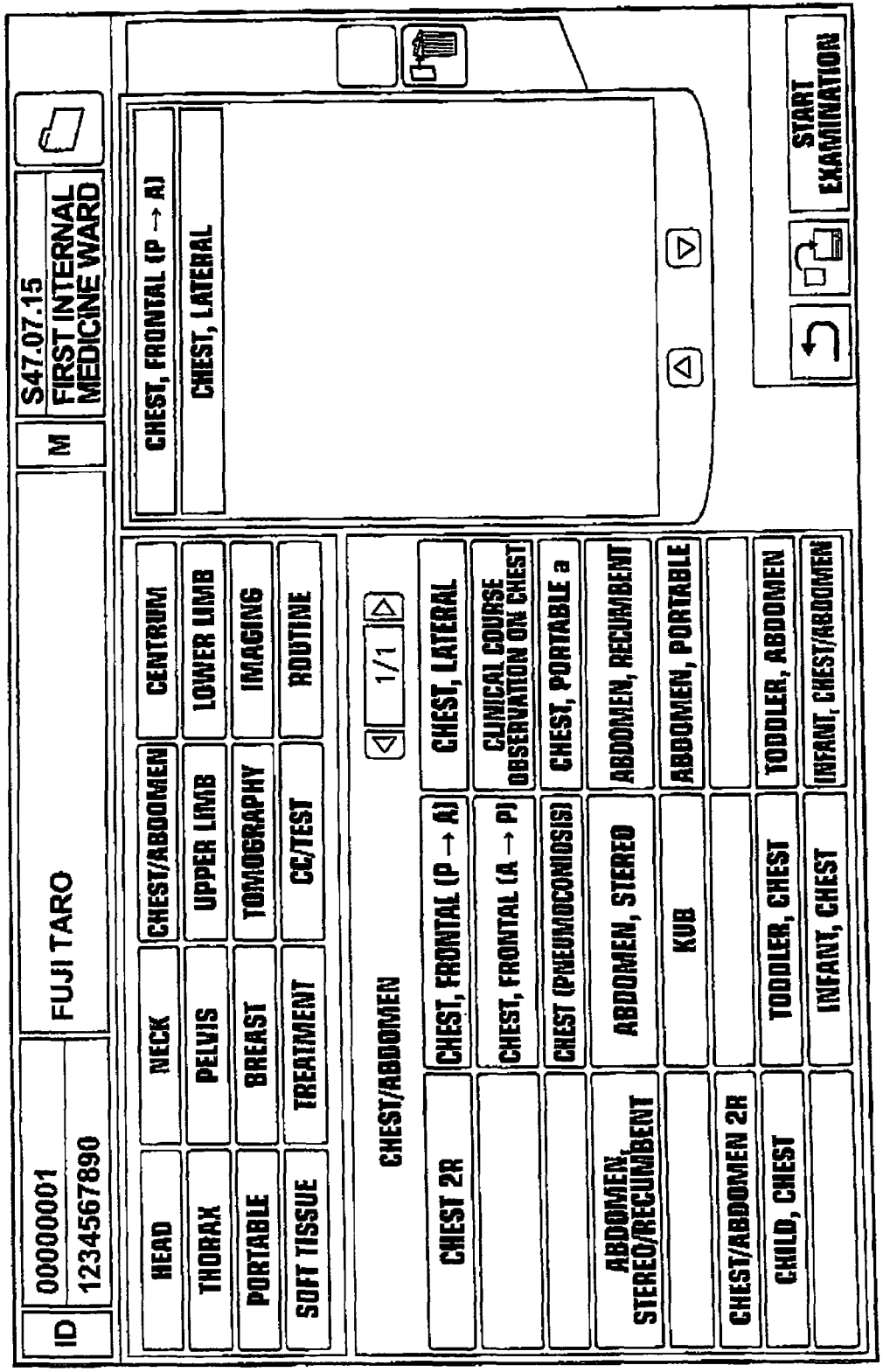
FIG. 3 shows an example of imaging menus.

Hereinafter, an embodiment of the present invention will be described with reference to the accompanying drawings.

As shown in FIG. 1, a medical system in a medical institution comprises an imaging apparatus 2 such as a CR (Computed Radiography) apparatus for obtaining a medical image, an image reproduction apparatus 1 installed in each ward (or for each physician or technician), and a network 3 such as a LAN for connecting the image reproduction apparatus 1 and the imaging apparatus 2. The medical image imaged by the imaging apparatus 2 is sent to the image reproduction apparatus 1 via the network 3.

As shown in FIG. 2, the image reproduction apparatus 1 comprises medical image input means 10, imaging menu display means 20, imaging menu acceptance means 30, image processing means 40, reproduction means 50, index value calculation means 60, judgment means 70, and warning means 80. The medical image input means 10 inputs the medical image obtained by imaging of a subject. The imaging menu display means 20 displays a imaging menu. The imaging menu acceptance means 30 accepts selection of an imaging menu item from the imaging menu. The image processing means 40 carries out image processing on the medical image to convert the medical image into an image appropriate for reproduction according to the selected imaging menu item. The reproduction means 50 reproduces the medical image having been subjected to the image processing on the screen of a CRT or the like. The index value calculation means 60 calculates an index value representing an anatomical characteristic of the medical image. The judgment means 70 judges the most appropriate imaging menu item to be selected from imaging menu items, based on the index value. The warning means 80 issues a warning in the case where the selected imaging menu item is not the most appropriate imaging menu item.

The medical image input means 10 inputs the medical image imaged by the imaging apparatus 2 such as a CR apparatus via the network 3 such as a LAN. Alternatively, the medical image input means may read the medical image stored in a recording medium.

As shown in FIG. 3, the imaging menu display means 20 displays imaging menu items related to imaged body parts, directions of imaging, the subject, and the like, as imaging menus. The imaging menu items related to the imaged body parts are "head", "chest/abdomen", and "breast", for example. After selection of the imaged body part has been completed, the imaging menu items related to the direction of imaging corresponding to the body part and the imaging menu items related to the subject are further displayed as lower-level imaging menus. For example, for a medical image obtained by X-ray imaging of a chest, if the item "chest/abdomen" is selected from the displayed imaging menu for the imaged body part, items such as "chest, frontal" and "chest, lateral" are displayed as the imaging menu items for the radiography direction related to imaging of chest/abdomen. Furthermore, for the case of chest radiography, the imaging menu items related to the subject are displayed for selecting whether the subject is an "infant", or a "toddler" or a "child", since air content in the subject's lungs becomes different depending on whether the subject is an adult, a child, a toddler, or an infant. The respective categories such as the imaged body part, the imaging direction, and the subject have the plurality of imaging menu items belonging thereto, and the items belonging to the same category are subjected to exclusive selection. Therefore, any two of items of the same category cannot be selected together. However, if the subject is an adult, none of the imaging menu items related to the subject, that is, the items "infant", "toddler", and "child" is selected. Therefore, in some cases, none of the imaging menu items belonging to the same category may be selected.

The imaging menu acceptance means 30 accepts the imaging menu items selected by the user using input means 32 such as a pointing device or a keyboard while viewing the imaging menu items displayed as the imaging menus on the screen.

The reproduction means 50 displays and reproduces the medical image on the screen of the LCD or CRT so that an image interpreter such as a physician can observe the medical image. At this time, in order to cause the displayed medical image to become appropriate for image interpretation, the image is displayed after the image processing means 40 has carried out the image processing such as density adjustment processing or frequency enhancement processing thereon.

The image processing means 40 carries out the image processing on the medical image for converting the medical image into an image appropriate for diagnosis according to the selected imaging menu items. For example, in the case where the medical image is a chest radiograph, the image tends to have low contrast due to smaller air content in the subject's lungs if the subject is an infant, a toddler, or a child. Therefore, in the case where the medical image is a chest radiograph of the subject as an infant, a toddler, or a child, density adjustment processing is carried out for enhancing the contrast of the image. Alternatively, an organ (such as bones) as a target of diagnosis may be enhanced through frequency enhancement processing or the like.

The index value calculation means 60 calculates the index value representing an anatomical characteristic of the medical image. The judgment means 70 judges the most appropriate imaging menu item from the corresponding imaging menu based on the calculated index value.

Reproduction by the image reproduction apparatus 1 on the screen of LCD or CRT will be described next according to a flow chart shown in FIG. 4, by using the medical image as a chest X-ray image obtained through X-ray imaging of a chest with a CR apparatus.

A medical image 100 obtained by imaging of the chest of the subject with the CR apparatus (hereinafter referred to as the chest X-ray image 100) is sent to the image reproduction apparatus 1 via the network 3. The image reproduction apparatus 1 inputs the chest X-ray image 100 from the medical image input means 10 (S100).

The user selects the imaging menu item related to the imaged body part while using the input means 32 such as the pointing device, from the imaging menu such as the menu shown in FIG. 3 displayed by the imaging menu display means 20, upon reproduction of the input chest X-ray image 100 by the reproduction means 50. For the chest X-ray image, the item "chest/abdomen" is selected as the imaged body part. In the case of a chest X-ray image, air content in lung fields is smaller for an infant, a toddler, or child than for an adult, leading to unclear contrast between the lung fields and surrounding tissues. Therefore, in the case where the subject is not an adult, the image processing such as density adjustment needs to be carried out before display and reproduction of the image by using an appropriate parameter according to the imaging menu item such as "infant", or "toddler", or "child" selected from the imaging menu, for converting the image into an image with high contrast that is appropriate for interpreting. For this reason, after the item "chest/abdomen" has been selected as the imaged body part, the imaging menu display means 20 displays the items "infant", or "toddler", or "child" as the detailed imaging menu items. The user then selects the corresponding one of the items representing the imaged subject of the chest X-ray image 100 by using the input means 32 (S101).

In the case where any one of the items "infant", "toddler", and "child" has been selected, the image processing means 40 carries out the density adjustment processing or the like on the chest X-ray image 100 for causing the contrast to become clear between the lung fields and the surrounding tissues, since air content in the lung fields is smaller in the chest X-ray image thereof than a chest X-ray image of an adult. In this manner, the image processing means 40 converts the chest X-ray image 100 into the image appropriate for interpreting by sharpening the contrast. The reproduction means 50 reproduces the chest X-ray image 100 having been subjected to the image processing on the screen (S102).

In the case where none of the items "infant", "toddler", and "child" has been selected from the menu shown by the imaging menu display means 20 although the subject was actually an infant, or a toddler, or a child, the chest X-ray image 100 without the density adjustment is reproduced by the reproduction means 50. Consequently, the image is displayed on the screen in a state that is not appropriate for interpreting due to the low contrast.

Therefore, the index value calculation means 60 calculates the index value representing an anatomical characteristic of the chest X-ray image 100 being displayed (S103), and the judgment means 70 judges the most appropriate imaging menu item from the imaging menu, based on the calculated index value (S104).

More specifically, the index value calculation means 60 detects a thoracic region (or lung-field regions) in the chest X-ray image 100, and finds the index value representing whether the subject is an adult, an infant, a toddler, or a child, based on a size of the region.

For example, an approximate thorax outline is extracted from the chest X-ray image 100 by use of an edge detection mask such as a Gabor function. An approximate position of the center of the extracted thorax is found, and conversion into polar coordinates is carried out around the position as a reference point of the conversion. A thorax outline is then automatically detected through template matching processing using a template as a reference having a shape that is substantially the same as an average thorax outline, in a polar coordinate plane (see Japanese Unexamined Patent Publication No. 2003-006661 filed by the assignee, for example).

Alternatively, threshold values for determining positions outside lung-field regions are found based on an average profile of pixel values of a plurality of chest X-ray images as a reference. Positions exceeding the threshold values are searched for from center regions of the right and left lung fields toward the outside of the chest X-ray image 100. The positions exceeding the threshold values are then determined to represent the outside of the lung fields, for detecting the thoracic region of the chest X-ray image 100 (see U.S. Patent Application Publication No. 20020072665, for example).

The index value calculation means 60 calculates the size of the thoracic region detected in this manner, and uses the size as the index value. Based on the index value, the judgment means 70 judges whether the subject is an adult, an infant, a toddler, or a child, and judges the imaging menu item corresponding to a result of the judgment as the most appropriate imaging menu item.

Alternatively, a thickness of ribs may be found as the index value. More specifically, entire rib shapes can be detected according to a Hough transform for parabola detection or an edge detection filter described in Peter de Souza, "Automatic Rib Detection in Chest Radiographs", Computer Vision, Graphics and Image Processing 23, pp. 129-161, 1983", for example. Furthermore, rib shapes may be detected in a plurality of chest X-ray images representing normal chests for generating a model rib shape, according to which the rib shapes of the subject in the chest X-ray image 100 can be inferred (see Japanese Unexamined Patent Publication No. 2005-198887 filed by the assignee, for example).

The index value calculation means 60 calculates the thickness of ribs as the index value from the rib shapes obtained in this manner. The judgment means 70 judges whether the subject is an adult, an infant, a toddler, or a child, based on the index value (the rib thickness), and judges the most appropriate imaging menu item corresponding to a result of the judgment among the imaging menu items related to the subject.

In the case where the most appropriate imaging menu item judged in this manner does not agree with the imaging menu item selected by the user (S105), the warning means 80 alerts the user by displaying warning on the screen, for example (S106). Alternatively, other means such as sound may be used, instead of display of the warning.

As shown by a flow chart shown in FIG. 5, in the case where the most appropriate imaging menu item judged by the judgment means 70 does not agree with the imaging menu item selected by the user, the imaging menu item selected from the imaging menu being displayed may be changed automatically to the most appropriate imaging menu item, and the imaging menu acceptance means 30 accepts the most appropriate imaging menu item as the selected imaging menu item (S107). The image processing means 40 then carries out the image processing corresponding to the most appropriate imaging menu item on the chest X-ray image 100, for reproduction of the image 100 by the reproduction means 50 (S108).

As has been described above, by detecting an anatomical characteristic in the medical image for judging whether the imaging menu item selected by the user is the most appropriate imaging menu item, erroneous selection by the user can be lessened.

In the above embodiment, the case has been described where the chest X-ray image is imaged from the front and judgment is made as to whether the subject is an adult, an infant, a toddler, or a child. In the case where the medical image is a chest X-ray image imaged from a side instead of from the front, only one lung region is detected. Therefore, the imaging direction can be judged between the front and the side. For this reason, in the case where the user has selected the item "frontal" from the corresponding imaging menu, warning may be carried out for alerting the user to the direction that should be "lateral".

In the above embodiment, the case of the chest X-ray image has been described. In the case where an image is a mammogram but a user has selected "chest/abdomen" from the corresponding imaging menu, the most appropriate imaging menu item may be judged by finding an index value representing an anatomical characteristic such as an outline shape or size of an imaged subject if no thoracic region is detected.

The density adjustment processing has been described as the image processing in the above embodiment. However, the image processing may be frequency enhancement processing and carried out on the medical image for enhancing bones or soft tissues upon necessity.

What is claimed is:

1. An image reproduction apparatus comprising:
    means for inputting a medical image of a subject's chest obtained by radiographic imaging;
    means for displaying an imaging menu including exclusively selectable imaging menu items regarding imaging information of the medical image;
    means for accepting selection of the imaging menu items from the displayed imaging menu;
    means for carrying out image processing on the medical image to convert the medical image into an image appropriate for reproduction according to the selected imaging menu item;
    means for reproducing the medical image having been subjected to the image processing;
    means for calculating an index value representing a thickness of a rib in the medical image;
    means for determining an age of the imaged subject based on the calculated index value; and
    means for judging the most appropriate imaging menu item to be selected from the imaging menu items according to the determined age.

2. The image reproduction apparatus according to claim 1, wherein
    the selection of the imaging menu items in the imaging menu being displayed is accepted from a user input means, and
    the image reproduction apparatus further comprises a means for carrying out warning in the case where the selected imaging menu item is not the most appropriate imaging menu item having been judged.

3. The image reproduction apparatus according claim 1, wherein the imaging menu item judged most appropriate is accepted as the selected imaging menu item.

4. The image reproduction apparatus according to claim 1 wherein the image processing is density adjustment processing.

5. The image reproduction apparatus according to claim 1 wherein the image processing is frequency enhancement processing.

6. The apparatus of claim 1, wherein the thickness of the rib is determined from a dimensional shape of the rib.

7. A non-transitory computer-readable medium encoded with a computer program for causing a computer to perform the functions as:
    means for inputting a medical image of a subject's chest obtained by radiographic imaging;
    means for displaying an imaging menu including exclusively selectable imaging menu items regarding imaging information of the medical image;
    means for accepting selection of the imaging menu items from the displayed imaging menu;
    means for carrying out image processing on the medical image to convert the medical image into an image appropriate for reproduction according to the selected imaging menu item;
    means for reproducing the medical image having been subjected to the image processing;
    means for calculating an index value representing a thickness of a rib in the medical image;
    means for determining an age of the imaged subject based on the calculated index value; and
    means for judging the most appropriate imaging menu item to be selected from the imaging menu items according to the determined age.

* * * * *